(12) United States Patent
Johansson et al.

(10) Patent No.: US 10,028,808 B2
(45) Date of Patent: Jul. 24, 2018

(54) TRAY SYSTEM AND METHOD OF PREPARING A CUSTOMIZED INFORMATION SHEET

(71) Applicant: DENTSPLY International Inc., York, PA (US)

(72) Inventors: Anders Johansson, Göteborg (SE); Johan Bergelin, Lilla Edet (SE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 13/960,962

(22) Filed: Aug. 7, 2013

(65) Prior Publication Data

US 2014/0170592 A1   Jun. 19, 2014

Related U.S. Application Data

(60) Provisional application No. 61/692,786, filed on Aug. 24, 2012.

(30) Foreign Application Priority Data

Aug. 15, 2012  (EP) .................................... 12180535

(51) Int. Cl.
| | |
|---|---|
| *B65D 83/10* | (2006.01) |
| *A61C 8/00* | (2006.01) |
| *A61C 3/04* | (2006.01) |
| *A61C 19/02* | (2006.01) |

(52) U.S. Cl.
CPC .............. *A61C 8/0087* (2013.01); *A61C 3/04* (2013.01); *A61C 19/02* (2013.01); *Y10T 29/49826* (2015.01)

(58) Field of Classification Search
USPC .................... 206/370, 368, 438, 63.5, 459.5
See application file for complete search history.

(56) References Cited

U.S. PATENT DOCUMENTS

| | | | | |
|---|---|---|---|---|
| 2,358,295 | A | * | 9/1944 | Bacigalupi ........... B65D 5/5038 164/DIG. 10 |
| 2,828,047 | A | * | 3/1958 | Weiselberg ........ B65D 71/0029 126/9 A |
| 3,743,088 | A | * | 7/1973 | Henkin ......................... 206/569 |
| 3,878,939 | A | * | 4/1975 | Wilcox ......................... 206/373 |

(Continued)

OTHER PUBLICATIONS

European Search Report, Application No. 12180535.2, Published Jan. 30, 2013.

(Continued)

*Primary Examiner* — Jacob K Ackun
(74) *Attorney, Agent, or Firm* — Dentsplay Sirona Inc.

(57) ABSTRACT

The invention discloses a tray system and a method for preparing such tray system. The tray system including a tray with a base having holding arrangements for holding implant components, instruments and/or instrument holders, at least a first and a second information sheet which both are adapted to be independently removably arranged on said base of said tray. Each information sheet has its own distribution of holes, which are placed in register with the holding arrangements of the base when the information sheet is arranged on the base, so that an implant component, instrument or instrument holder is arrangable into one of said holing arrangements through a respective one of said holes.

5 Claims, 7 Drawing Sheets

(56) References Cited

U.S. PATENT DOCUMENTS

| | | | | |
|---|---|---|---|---|
| 4,155,446 A * | 5/1979 | Aronson | ............... | 206/214 |
| 4,823,959 A * | 4/1989 | Bixler | ............... | 206/562 |
| 5,047,019 A * | 9/1991 | Sincock | ............... | A61M 5/3213 |
| | | | | 206/366 |
| 5,394,983 A * | 3/1995 | Latulippe et al. | ............... | 206/370 |
| 5,525,314 A | 6/1996 | Harson | | |
| 6,164,448 A * | 12/2000 | Schmutz | ............... | H05K 13/0084 |
| | | | | 206/488 |
| 6,561,353 B2 * | 5/2003 | Levieux | ............... | A47G 7/025 |
| | | | | 206/423 |
| 6,651,836 B1 * | 11/2003 | Hofheins | ............... | A47G 19/06 |
| | | | | 206/562 |
| 7,410,053 B2 * | 8/2008 | Bowen et al. | ............... | 206/373 |
| 7,871,050 B2 * | 1/2011 | Epstein | ............... | 248/311.2 |
| 8,336,708 B2 * | 12/2012 | Potterfield et al. | ............... | 206/373 |
| 8,893,885 B2 * | 11/2014 | Hutchens | ............... | 206/373 |
| 8,899,417 B1 * | 12/2014 | Chen | ............... | B25H 3/003 |
| | | | | 206/372 |
| 2004/0099567 A1 * | 5/2004 | Frank | ............... | A47G 29/08 |
| | | | | 206/562 |
| 2005/0133394 A1 * | 6/2005 | Liu | ............... | A45C 11/00 |
| | | | | 206/349 |
| 2008/0156671 A1 * | 7/2008 | Jansson | ............... | 206/216 |
| 2011/0132911 A1 * | 6/2011 | Zhang et al. | ............... | 220/507 |
| 2012/0094249 A1 | 4/2012 | Abene et al. | | |

OTHER PUBLICATIONS

International Search Report, Application No. 2013/066585, Published Aug. 7, 2013.
International Written Opinion, Application No. 2013/066585, Published Aug. 7, 2013.

* cited by examiner

TRAY SYSTEM AND METHOD OF PREPARING A CUSTOMIZED INFORMATION SHEET

CROSS-REFERENCE TO RELATED APPLICATIONS

This patent application claims the benefit of and priority to EP Application Ser No. 12180535.2, filed on Aug. 15, 2012 and U.S. Provisional Patent Application Ser. No. 61/692,786, filed on Aug. 24, 2012, which are herein incorporated by reference for all purposes.

FIELD OF THE INVENTION

The present invention relates to a tray system comprising a tray with a base having holding arrangements for holding implant components, instruments and/or instrument holders.

The present invention further relates to a method of preparing a customized information sheet for a tray with a base having holding arrangements in a specific pattern for holding implant components, instruments and/or instrument holders.

TECHNICAL BACKGROUND

During surgical operations, for example dental surgical operations, different kinds of instruments may be used. The instruments are often arranged to a tray in a specific position in order to help the surgeon to find the right instrument fast. The tray may be provided with instrument holders, for example a hole with a grommet arranged therein. Next to each holder an information text or an identifying colour may be printed on the tray in order to make it easier to find the correct instrument for a certain operation. Sometimes the instrument providers gives the instruments to be used in a specific surgical operation a certain colour. The text and the colour on the tray may correspond to the colour on the instrument.

Before the surgical operation, for example a dental surgical operation, the surgical tray is prepared with, for example, different drills and the implants to be used. A custom drilling and installation protocol may state what implants, drills and implants holders to use in each specific osteotomy. The correct drills and implants are then arranged to the tray according to the protocol and in the right holders according to the text on the tray. Hence, for each specific situation, i.e. implant type, size etc., the tray is loaded differently.

As much as the printed information and colour helps the surgeon it may also be a problem since too much information may be annoying or confusing, especially if some of the information is not relevant to the particular osteotomy to be performed.

Further, if instruments are used from another provider than the one providing the tray, the text and colour on the tray may not correspond to the colour or the order of the instruments to be used and is then more confusing than helping.

Hence, there is a need to improve surgical trays.

SUMMARY OF THE INVENTION

The object of the present invention is to provide a tray system that overcomes the above issues.

The invention is based on the insight that by allowing the information associated with holders in a tray to be separated from those holders, a more flexible tray system may be provided. The inventors have also realized that by providing the option of concealing some of the holders and reducing the information, the user may be faced with only such information which he/she needs for a particular surgery.

According to a first aspect of the invention this is accomplished by a tray system comprising a tray with a base having holding arrangements for holding implant components, instruments and/or instrument holders, at least a first and a second information sheet which both are adapted to be independently removably arranged on said base of said tray, wherein said first sheet is replaceable by said second sheet and vice versa, said first sheet comprises a first set of holes having a first distribution and said second sheet comprises a second set of holes having a second distribution, which is different compared to the first distribution, wherein when said first sheet is arranged on said base of said tray each one of said first set of holes in said first sheets is located in register with a respective one of said holding arrangements so that an implant component, instrument or instrument holder is arrangable into one of said holding arrangements through a respective one of said first set of holes and when said second sheet is arranged on said base of said tray each one of said second set of holes in said second sheet is located in register with a respective one of said holding arrangements so that an implant component, instrument or instrument holder is arrangable into one of said holding arrangements through a respective one of said second set of holes.

By having two information sheets, each having a different set of holes, the user can choose the one suitable for a specific situation. Instead of having a lot of holes in the tray, with all kind of information on it, the user can arrange a separate sheet on the tray which is suitable for a specific use which makes it easier for the user to arrange the right component on the tray and then find it again during surgery. The next time the tray shall be used, for example, for a different surgical operation than the previous one, the second sheet may be used having a hole distribution which is more appropriate for that specific situation.

By having separate information sheets, instead of a tray with all kinds of fixed information the user may design his own sheet. This way the user can get a tray system which is adapted to his or hers specific needs. When the first information sheet is arranged on the base of the tray, the holes in the first information sheet may be in register with some holding arrangements in said base, while when the second information sheet is arranged on the base of the tray the holes in the second information sheet may be in register with completely different holding arrangements in said base. Alternatively, some of the holes of the first and the second sheets may be in register with the same holding arrangements, and the second sheet may for example have additional holes which are in register with other holding arrangements.

According to at least one exemplary embodiment said at least one of said first sheet and said second sheet comprises a coloured area and/or information text next to at least one of the holes. Information text and coloured areas may help the user to organise the objects to be arranged in the holding arrangements. It may also help the user to find the right object and/or the objects which belong to each other. For a specific implant a special drill or special drills and/or tools may have to be used and they can then be identified with colours and text, i.e. they may be colour coded. For example, for a dental implant having a diameter of 3.5 mm all relevant drills and tools may be marked in a specific colour, for example in red, and they may then be arranged in an area on the sheet which has a red marking. Another dental implant, for example having a diameter of 4.0 mm, may be associated with a different colour, for example yellow. Text information and/or FIGURES may help the user further to organise the objects in the right place and help the user to find the correct objects.

The information text and/or coloured area, i.e. the information markings, may be printed or attached to the sheet by a stick-on-label or it may be in-mould decoration or in-mould labelling in the sheet.

According to at least one exemplary embodiment said at least one of said holes in said first set of holes and/or said second set of holes is larger in cross-section than the holding arrangement it is in register with. By having a holes larger in cross-section than the cross-section of the holding arrangement with which it is in register, it is easy to arrange a component into the holding arrangement.

According to at least one exemplary embodiment said first sheet and/or said second sheet are arrangable to said tray by a snap locking arrangement. Snap locking arrangements are easy fasteners, i.e. they are often easy to arrange and may be designed to be easy to remove. A snap locking arrangement may be a snap catch arranged on the sheet and which snaps into an opening in the tray. Another alternative may be a snap catch on the tray which snaps into a hole in the sheet or alternative over the edge of the sheet. As an alternative the sheets may only be loosely placed on the tray.

According to at least one exemplary embodiment at least one of said holding arrangements is an aperture in said base. An aperture in the base is a cost effective way to make a holding arrangement.

For example, the aperture may be a through hole. The through hole may be fitted for example with a grommet which may hold the objects. The aperture has preferably a round shape. By having through holes it is possible to permit steam or other sterilant to pass through the sheet if it is sterilized in the closed tray.

According to at least one exemplary embodiment said holding arrangement comprises flexible protrusions arranged circumferentially around a centre axis of the holding arrangement. They are preferably evenly distributed around the holding arrangement.

According to at least one exemplary embodiment said flexible protrusions are protruding in the opposite direction to the side of the base on which the sheets are arrangeable and the through hole has a cross-sectional area at the side of the base on which the sheets are arrangeable which is larger than a cross-sectional area of the through hole at the end of the flexible protrusion. Flexible protrusions together with a larger open cross-sectional area at the top than at the end of the flexible protrusions have the advantage that the flexible protrusions may bend away when a tool or an implant is arranged in the holding arrangement. This way differently sized tools and implants can be fitted within the holding arrangement. The change of area may be accomplished by the flexible protrusions slightly protruding downwards and towards the centre axis of the holding arrangement. According to at least one exemplary embodiment they may be slanting towards the centre axis of the holding arrangement. The flexible protrusions may then be also slanted in the direction towards the centre axis and/or they may be parallel with the centre axis. All flexible protrusions may be the same or they may be differently designed. According to at least one exemplary embodiment the holding arrangement comprises three flexible protrusions. There may however be more or less.

According to at least one exemplary embodiment said first and/or second sheets are made of plastic or paper. The sheets may be made in a material which can be sterilized and/or disinfected for example plastic. As an alternative the sheet may be a disposable sheet which can be thrown away. Preferably, the sheet is relatively rigid. The thickness of the sheet is preferably not thicker than the tools and/or parts which shall be held in the holding arrangement, i.e. the tool or the part should protrude above the sheet so that the user easily can remove the tools/parts.

According to at least one exemplary embodiment said first or said second sheet is arrangable to said base adjacent to a third sheet. This can be an alternative to one large sheet. For example if a clinic would like to build its own sheet out of smaller module sheets.

According to a second aspect of the invention the object of the present invention is accomplished by a method of preparing a customized information sheet for a tray with a base having a pattern of holding arrangements for holding implant components, instruments and/or instrument holders, the method comprises the steps of gathering information regarding positions of a subset of holding arrangements to be used, producing a sheet with holes having corresponding positions of the subset of holding arrangements such that when said sheet is arranged on said base of said tray each one of said holes in said sheet is located in register with a respective one of said holding arrangements to be used so that an implant component, instrument or instrument holder is arrangable into one of said holding arrangements through a respective one of said holes.

By gathering information of the positions of the holding arrangements which shall be used and producing a sheet accordingly makes it possible to make customized sheets. The user may tell the producer of the sheets which holding arrangements he wants to use. This may for example be done over the Internet. The producers of the sheets can then make a sheet with holes in the right place. The user then gets a customized sheet. Another advantage of customized sheets is that they may be designed to support a different drilling protocol, procedure, treatment option or implant system, for example from another producer.

According to at least one exemplary embodiment said method further comprises the steps of gathering colour information and/or text information to be arranged on said sheet next to at least one of the holes and arranging said colour information and/or said text information on said sheet.

By gathering information on information markings from the end user it is possible to customize the sheet even further. The end user can get a sheet which is the most suitable for him/her. If you have a tray from one producer, which has a certain colour coding on the parts they are selling, and the end user wants to use implants and tools from a second producer having other colour codings than the one producing the tray then a sheet can be made which works with the second producers colour coding.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated. Other objectives, features and advantages of the present invention will appear from the following detailed disclosure, from the attached dependent claims as well as from the drawings.

BRIEF DESCRIPTION OF THE DRAWINGS

The above, as well as additional objects, features and advantages of the present invention, will be better understood through the following illustrative and non-limiting detailed description of exemplary embodiments of the present invention, with reference to the appended drawings, where the same reference numerals will be used for similar elements, wherein.

All the figures are highly schematic, not necessarily to scale, and they show only parts which are necessary in order to elucidate the invention, other parts being omitted or merely suggested.

DETAILED DESCRIPTION OF PREFERRED EMBODIMENTS

A currently preferred embodiment of the present invention will now be described in more detail, with reference to the accompanying drawings.

Figure 1:
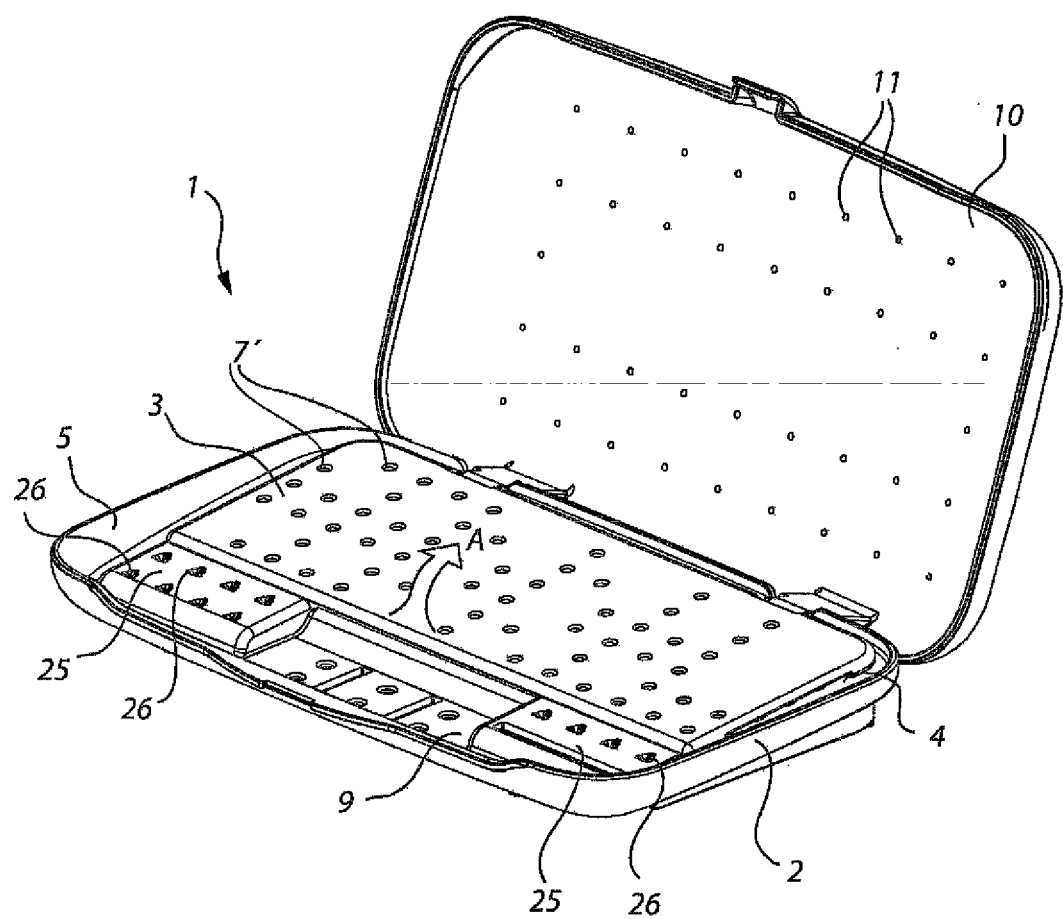
FIG. 1 shows in a perspective view a tray system according to at least one exemplary embodiment of the invention.
Figure 2:
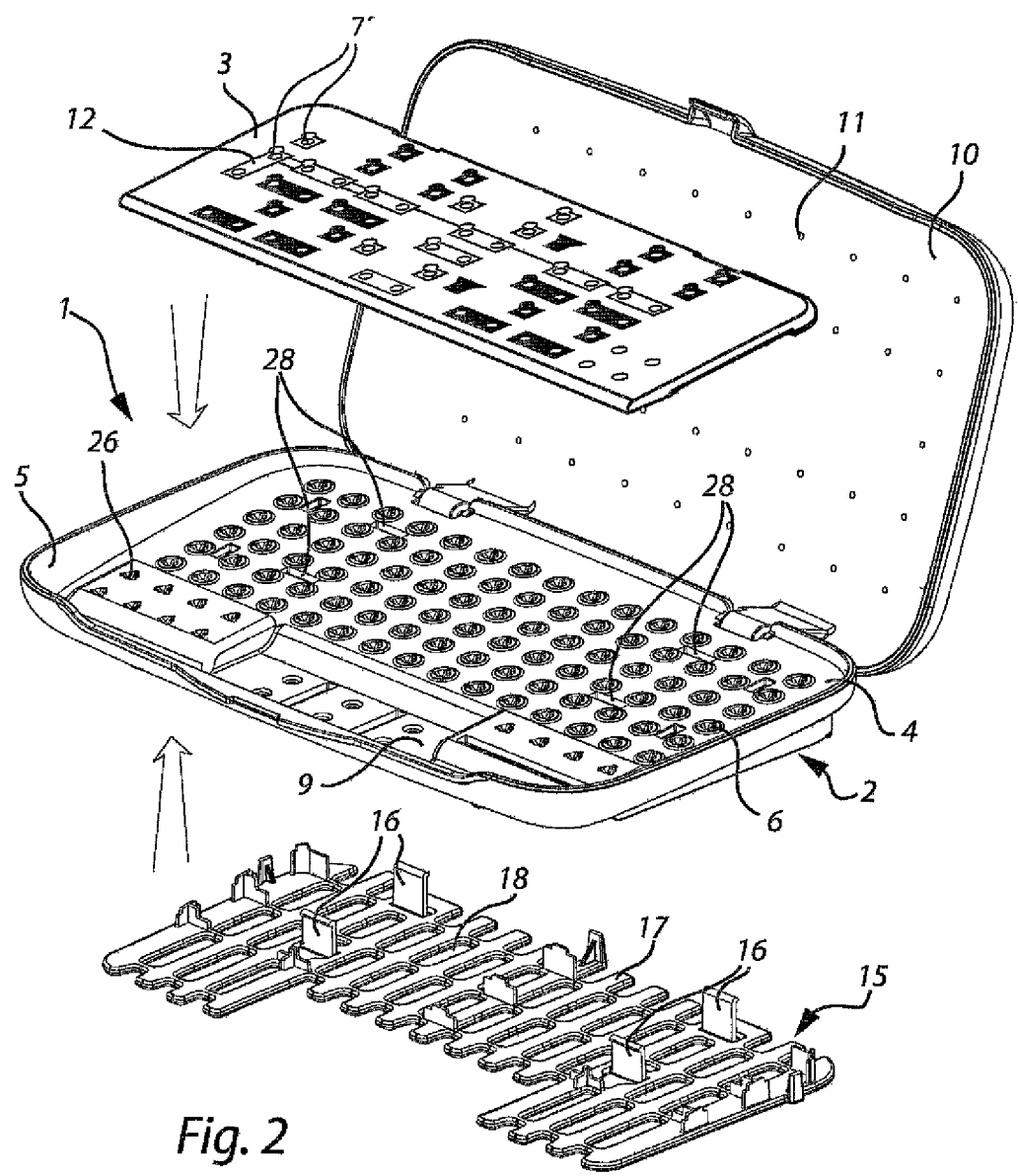
FIG. 2 shows in an exploded view in perspective a tray system according to at least one exemplary embodiment of the invention.

FIG. 1 and FIG. 2 show a tray system 1 which comprises a rectangular shaped tray 2 which has a base 4 and low side walls 5 all around. The tray is not limited to low side walls.

There might not be a side wall at all or it may be higher. The tray is also not limited to be a rectangular shaped tray. It may for example be round. On the base 4 is an information sheet 3 with information markings 12 (information markings not shown in FIG. 1) arranged.

The tray 2 is suitably made of plastic, however, it may be made of any kind of suitable material. Suitably, the tray is made of a material which can be disinfected and/or sterilized. The tray 2 is pivotally connected to a lid 10 which in a closed condition covers the base 4. Alternatively, the lid 10 is a separate lid. The lid 10 has openings 11 which permit steam or other sterilant to enter into and out of the tray system 1 when the lid 10 covers the tray 2, for example when the tray system 1 is being sterilized.

Figure 3:
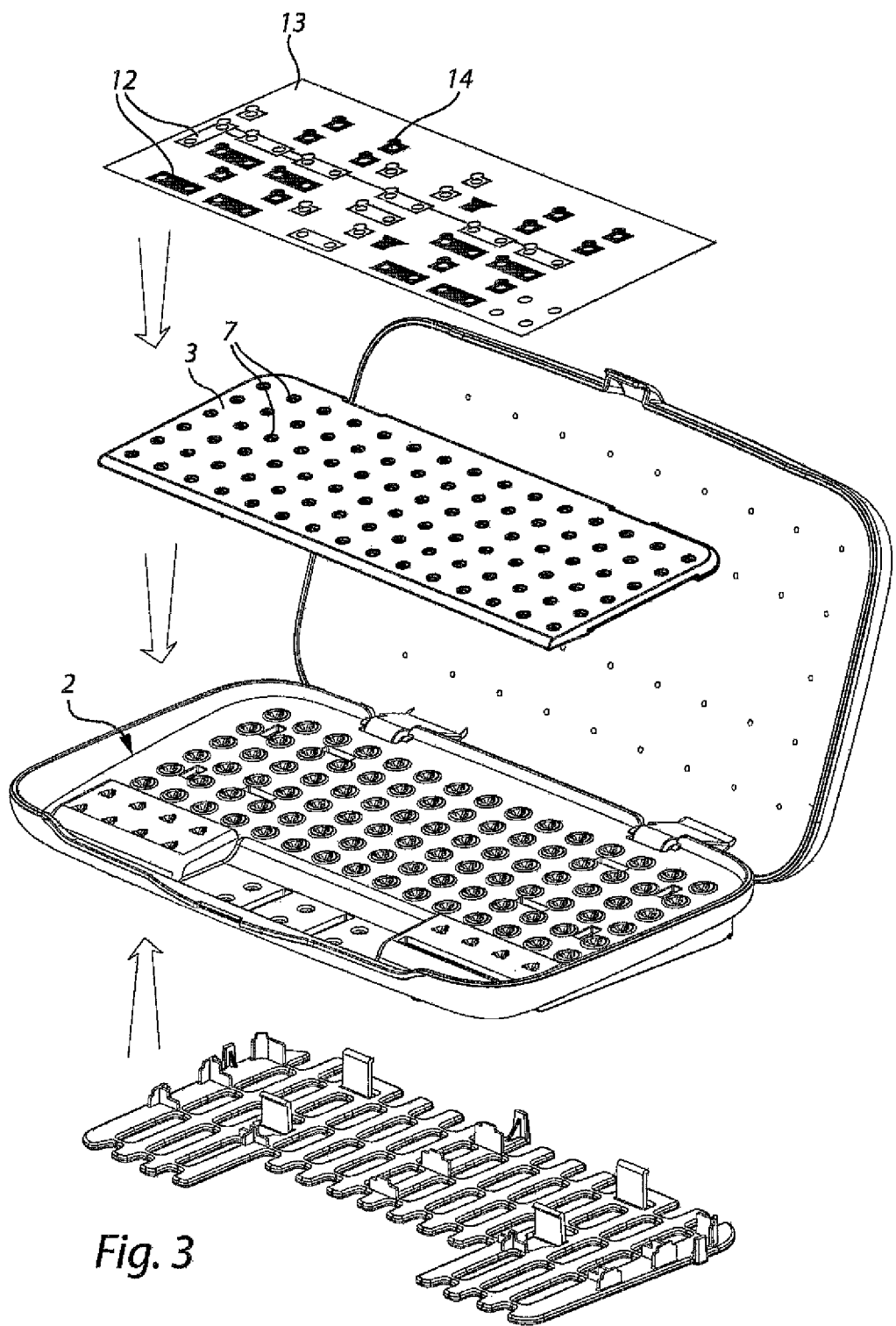
FIG. 3 shows in an exploded view in perspective a tray system according to at least another exemplary embodiment of the invention.

The sheet 3 may be a plastic sheet or a paper sheet or a sheet out of metal. Suitably, the sheet is relatively rigid. The thickness of the sheet is suitably not thicker than the tools and/or parts which shall be held in the tray, i.e. the tool or the part should protrude over the sheet 3 so that the user easily can remove the tools/parts. If the sheet 3 shall withstand to be disinfected and/or sterilized it is preferably made in a material suitable for this. On the sheet 3 information markings 12 are printed. As an alternative the information markings may be attached to the sheet by a stick on label 13 as shown in FIG. 3 or in-mould decoration or in-mould labelling.

The base 4 of the tray 2 comprises apertures 6, see FIG. 2, which are arranged in rows. These apertures 6 are holdings arrangements 6 for instruments, implants etc. As exemplified the holding arrangements 6 themselves are designed to hold an instrument, an instrument holder or a part to be implanted. The design will be discussed together in regard to the FIGS. 4-8. As an alternative a holding arrangement 6 may be a round through hole into which for example a known grommet can be inserted to hold the instrument.

The sheet 3 comprises a first set of holes 7' integrated in the sheet. The holes 7' are distributed over the sheet in a first distribution, i.e. a first pattern. The holes 7' on the sheet 3 are so arranged that when the sheet 3 is arranged on the base 4, each hole 7' on the sheet 3 is aligned with a respective aperture 6 on the tray 2, i.e. they are in register with each other.

Figure 9:
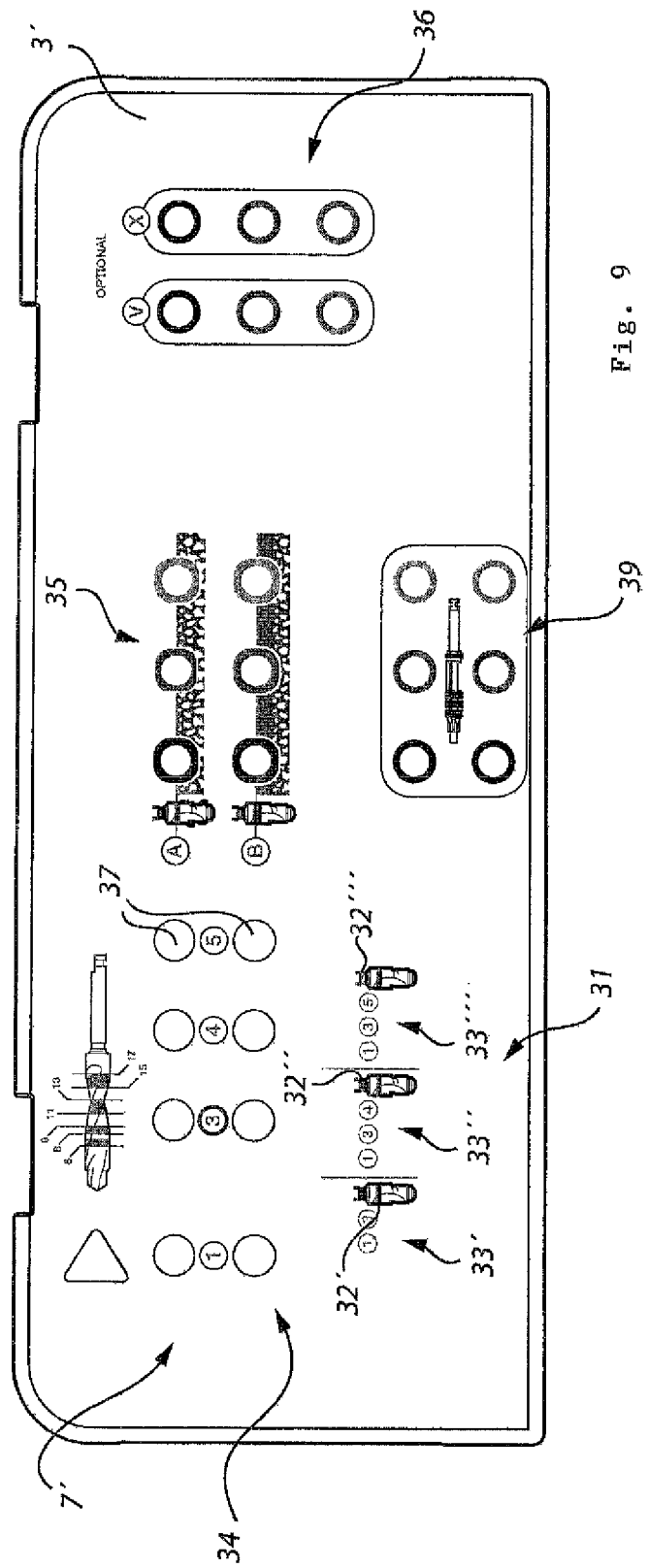
FIGS. 9 and 10 show two examples of different information sheets.
Figure 10:
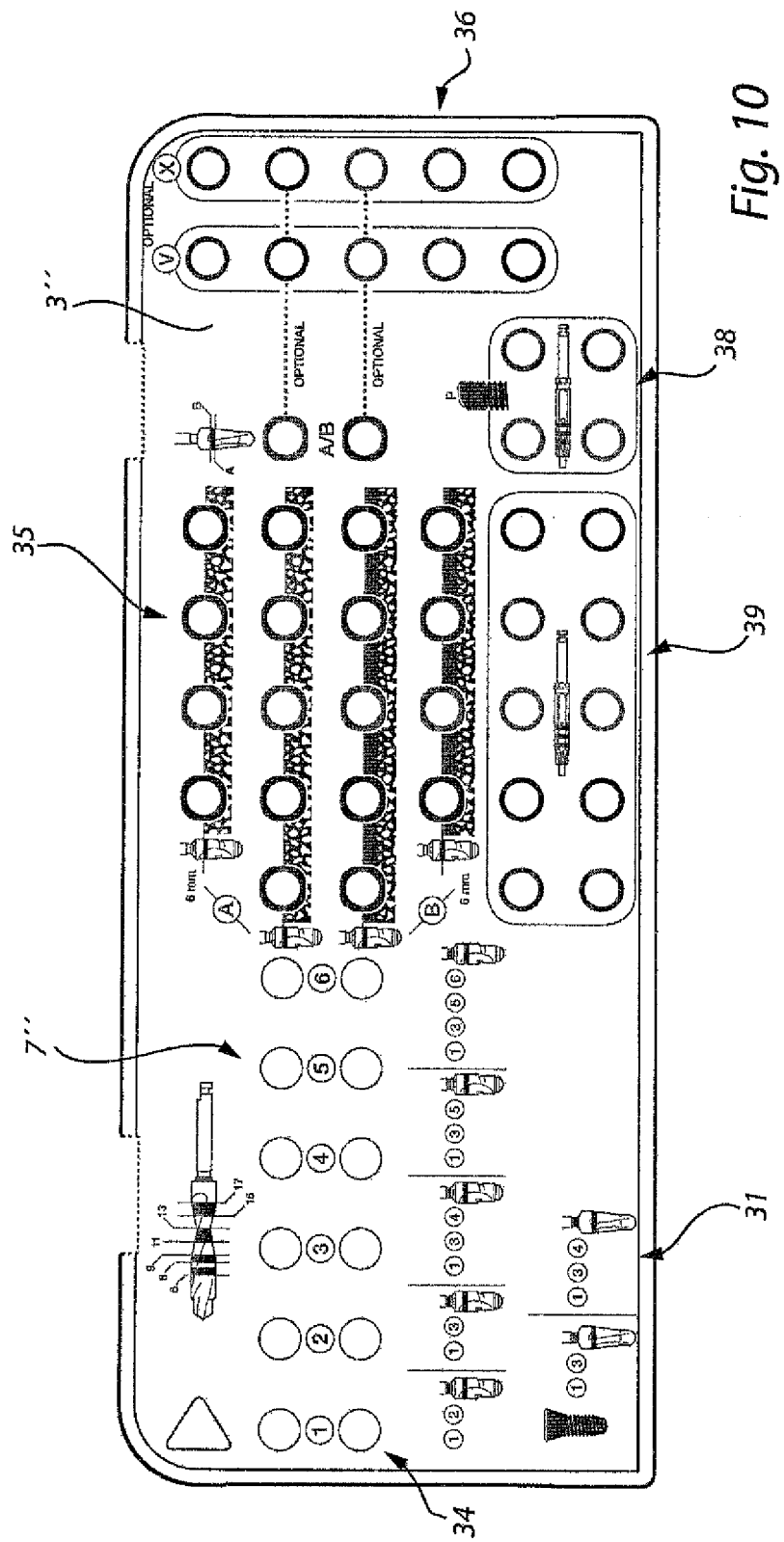

The sheet 3 is arranged to the tray 1 in a removable manner, in such a way that the sheet 3, which has a first distribution of holes, can be replaced by another sheet, i.e. a second sheet having a second set of hole distribution (see e.g. FIGS. 9 and 10). The sheets 3, 3', 3" may be snapped into place on the tray by a snap locking arrangement. For example a snap catch (or several) on the tray which snaps into a hole in the sheet or over the outer edge of the sheet (not shown).

The tray 2 has a lowered area 9, i.e. an area 9, which is below the base 4 of the tray. In this lowered area 9 other tools which are protocol independent can be stored. A silicon mat can be arranged in the lower area and longer instruments can be arranged thereon. Such an instrument may for example be a depth indicator or a wrench.

Further, this lowered area helps the user to grip the sheet 3, by allowing a finger or a finger tip to touch the side of the sheet 3 or underneath the sheet when the sheet 3 shall be removed. The sheet 2 may then be raised at one side in the direction of the arrow A (see FIG. 1).

The tray 2 has also two raised areas 25 with second holding arrangements 26 which may have a similar design as the holding arrangements 6. In these second holding arrangements 26 larger components, for example tools which are protocol independent, may be arranged.

The tray 2 also has slots 28 (see FIG. 2) in the base 4 for receiving a stand 15 with snap connections 16 which may snap into the slots 28. The stand 15 has a grid structure with apertures 18. When the stand 15 is arranged to the tray 2 the grid part 17 covers the holding arrangements 6. The grid part 17 will prevent water or sterilization agent to directly hit the parts stored in the holding arrangements when they are being disinfected and/or sterilized. Instead the agent will be directed around the part.

FIG. 3 shows the tray system 1 with a stick-on label 13 which shall be arranged on the sheet 3. The stick-on label 13 has a first distribution of openings 14. The sheet 3 is here exemplified as a sheet 3 with a lot more holes 7 than openings 14 on the label 13. Some of the holes 7 in the sheet 3 will be in register with the first distribution of openings 14 in the label 13 and the rest may be covered (concealed) by the label. The holes 7 not covered by the label is hence a first set of openings in the sheet having a first distribution i.e. a first pattern. Alternatively, the sheet 3 may have the same amount of holes and the same distribution as the stick-on label.

Figure 4:
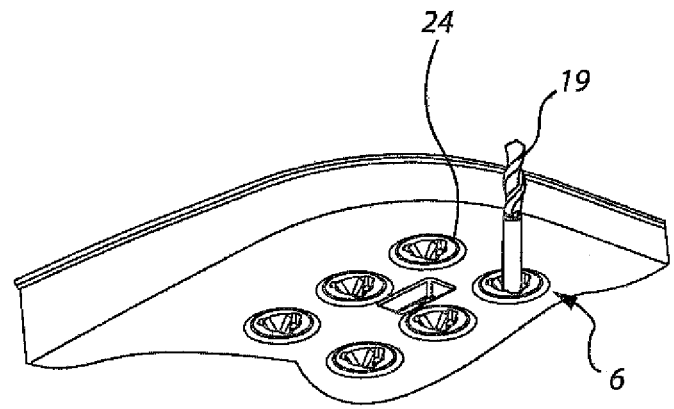
FIG. 4 shows a perspective view of some holding arrangements in a tray system with a tool arranged in one of the holding arrangement.
Figure 5:
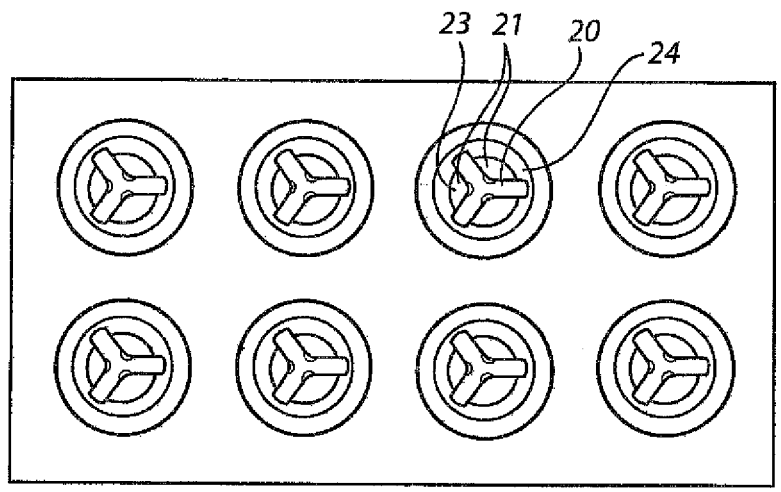
FIG. 5 shows some holding arrangements in the tray system shown in FIGS. 1-3 in a top view.

FIG. 4 shows a tool 19, i.e. a drill arranged in one of the holding arrangements 6.

Figure 6:
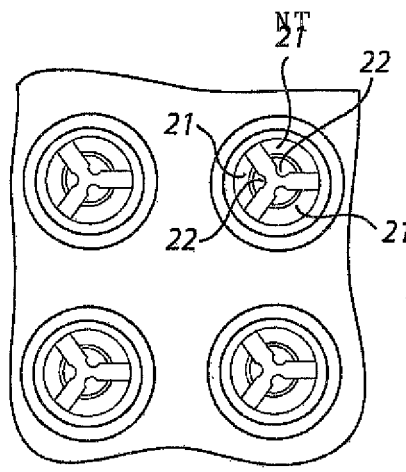
FIG. 6 shows the holding arrangements of FIG. 5 from a bottom view.
Figure 7:
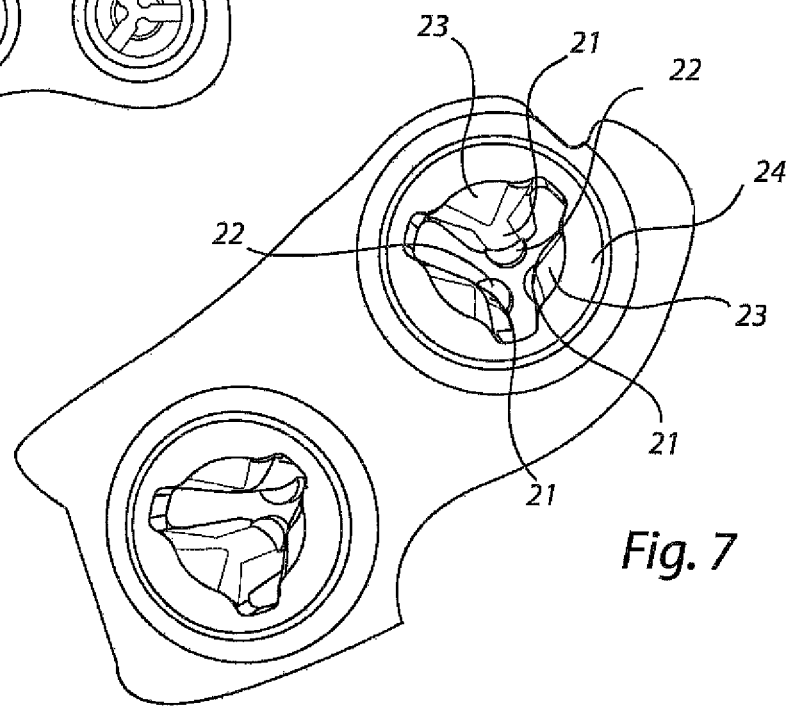
FIG. 7 shows the top view of FIG. 5 in perspective.
Figure 8:
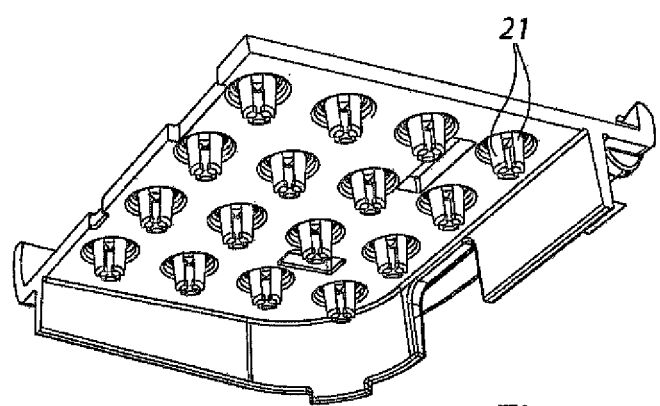
FIG. 8 shows the bottom view of FIG. 6 in perspective.

The holding arrangement 6 will now be described together with FIGS. 4, 5, 6, 7 and 8. The holding arrangement 6 when looking on the top of the tray (see FIG. 5) comprises of a through hole 20 which has a Y-shape. It gets its shape from three flexible protrusions 21, i.e.

holding protrusions 21, which are equally distributed around a centre point of the holding arrangement 6, protruding in the direction towards the underside of the tray (see also FIGS. 6, 7 and 8). These protrusions have a triangular shape when looking from the underside of the tray 2 (see FIG. 6.) with a round edge, so that all three protrusions forming an outer circularly shape. At the end of each protrusion is a nose 22 arranged which protrudes towards the centre point of the through hole 20 and it has a round shape.

That is, the flexible protrusions 21 are protruding in a direction opposite to the side of the base on which the sheet 3 is arrangeable and the through hole has a cross-sectional area at the side of the base on which the sheet is arrangeable which is larger than a cross-sectional area of the through hole at the end of the flexible protrusion. Flexible protrusions 21 together with a through hole having a larger open cross-sectional area at the top than at the end of the flexible protrusion have the advantage that the flexible protrusions may bend away when a tool or an implant is pressed into the holding arrangement 6. This way differently sized tools and implants can be fitted within the holding arrangements. The smaller open area is here accomplished by the protruding noses 22. When a component, for example a tool, which has a cross section which is larger than the cross sectional area at the end of the Y-shaped through hole at the nose 22, is inserted into a holding arrangement, the noses 22 of the holding protrusions will abut the tool on its outer contour and the holding protrusions 21 will slightly bend so that the tool can pass trough. The tool will be held by the three holding protrusions 21 which all press against the tool with their noses. Alternatively, the component may rest on the top of the protruding noses 22. The shape and the number of the flexible protrusions are not limited to the above. As an alternative the flexible protrusion may slant in the direction towards the centre axis.

In order to guide the component into the holding arrangement 6 the area 23 around the opening is slanted towards the centre point and it works as a guiding surface 23 and it has an inverted conical-shape. A circular area 24 around the holding arrangement 9 is raised. This can be done for design and/or production reasons. However, this area does not have to be raised.

FIG. 9 and FIG. 10 show two different sheets 3', 3" with different hole distribution patterns. These sheets are rectangular shaped and slightly smaller than the tray itself in order to fit on the rectangular shaped tray 2. However, if the tray has another shape, for example round the sheet may also have a round corresponding shape or another shape which fits onto the tray. Some of the holes, text and colour arrangements are distributed in the same manner in FIGS. 9 and 10, however the sheet in FIG. 10 has additional holes and text and some added colour scheme. Sheet 3' in FIG. 9 will now be discussed in detail, however the one disclosed in FIG. 10 works in a similar way. Sheet 3' comprises a first set of holes 7' and it has an cortical drill showing area 31 showing pictures and numbers of three different cortical drills 3.5, 4.0 and 4.5, the numbers referring to diameters in mm of associated implants. Each picture of the cortical drill is shown with a different colour on its neck 32', 32", 32''', which colour is the same colour as the implant to be implanted. Drill 3.5 has a black neck 32', drill 4.0 has a dark grey neck 32"and drill 4.5 has a light grey neck 32'''. Next to each drill picture is also a tool working plan 33', 33", 33''' arranged, which shows which tools to use for a certain implant and in which order. Above the cortical drill showing area 31 is a tool arrangement area 34 which comprises two rows with four openings 37 each (five in FIG. 10) and they are so arranged that columns are created. One row can be used for shorter tools and the other row for longer tools. Each column is numbered. Different tools, for example drills are arranged in the different holes. The numbers in the tool working plan 33', 33", 33''' next to the cortical drills pictures shows in which order the tools in the tool arrangement area 34 shall be used. For example, for dental implant 3.5 the tools in the tool arrangement area 34 in position 1 and 3 shall be used. Since position 2 will not be used with any one of the implants in the cortical drill showing area 31 in FIG. 9, that position has been omitted on sheet 3' in FIG. 9, but is present on sheet 3" in FIG. 10 since it is relevant for implant 3.0.

A second tool arrangement area 35 is arranged to the sheet also in two rows, row A for one type of bone quality and a second row B for a second type of bone quality and each three holes in each row has as a colour (black, dark gray and light gray) which corresponds to the colour of the implant. So after using the tools in the first tool arrangement area 34 the user might need other tools depending on the bone structure. The user then knows that for a 3.5 implant the tool placed in the black coloured hole shall be used. A third tool arrangement area 36 is also arranged where tools for very hard boned can be arranged and the colour also corresponds to the implants. A fourth tool arrangement area 39 is also arranged for placing implant drivers. The sheet in FIG. 10 shows a similar design, however having a different sets of holes 7" in the sheet 3" i.e. more cortical drills are shown in the cortical drill showing area 31 and hence more tools can be arranged in the first, third and fourth tool arrangement area 34, 36, 39 and the second tool arrangement area 35 have more options. Further, a fifth tool arrangement 38 area is arranged for a second type of implant, for example an implant driver for a sloped-top implant.

As an alternative to one large sheet two or more sheets may be arranged next to each other, for example if a clinic would like to build its own sheets out of smaller module sheets (not shown). If a dentist for example wants to work with a 3.0 implant he only has to take one small sheet. If he also wants to have a 3.5 implant he may arrange a second sheet for the 3.5 next to the sheet for a 3.0 implant.

The sheets 7', 7" are not limited to have this design. A user can design his own sheet, i.e. a customized information sheet wherein the provider of the sheet gathers information regarding positions of a subset of holding arrangements 6 the user wants to use. The provider of the sheet then produces a sheet with holes having corresponding positions of the subset of holding arrangements such that when the sheet is arranged on said base on said tray each one of said holes in said sheet is located in register with a respective one of said holding arrangements to be used so that an implant component, instrument or instrument holder is arrangable into one of said holding arrangements through a respective one of said holes. The provider of the sheet may then in a next step or in the same step gather colour information and/or text information to be arranged on the sheet next to at least one of the holes and the provider may then arrange the colour information and/or said text information on the sheet.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A tray system comprising
a tray with a base having a tool holding arrangement that includes a plurality of apertures for receiving and holding implant components, instruments and/or instrument holders;
at least a first and a second information sheet, which both are adapted to be independently removably arranged on said base of said tray, wherein said first sheet is replaceable by said second sheet on said tool holding arrangement and vice versa;
said first sheet including a first set of holes having a first distribution; and
said second sheet including a second set of holes having a second distribution, which is different compared to the first distribution;
wherein when said first sheet is arranged on said tool holding arrangement of said base of said tray, each one of said first set of holes in said first sheets is located in register with a respective one of said plurality of apertures of said tool holding arrangement so that an implant component, instrument or instrument holder is arrangable into one of said plurality of apertures of said tool holding arrangement through a respective one of said first set of holes;
wherein when said second sheet is arranged on said tool holding arrangement of said base of said tray, each one of said second set of holes in said second sheet is located in register with a respective one of said plurality of apertures of said tool holding arrangement so that an implant component, instrument or instrument holder is arrangable into one of said plurality of apertures of said tool holding arrangement through a respective one of said second set of holes;
wherein each aperture is a through hole with flexible protrusions distributed around a center point of the aperture, each protrusion having an end portion which protrudes towards the center point of the through hole and in the direction towards the underside of the tray,
wherein the flexible protrusions are protruding in a direction opposite to a side of the base on which the first sheet or the second sheet is arrangeable and the through hole has a cross-sectional area at the side of the base on which the first sheet or the second sheet is arrangeable which is larger than a cross-sectional area of the through hole at the end of the flexible protrusion, the flexible protrusions bendable in a direction away from the center point when the implant component, instrument or instrument holder is pressed into the holding arrangement; and,
wherein one of said sheets carries a tool working plan which shows which tools are used in which order.

2. A tray system according to claim 1, wherein at least one of said first sheet and said second sheet includes a colored area and/or information text next to at least one of the holes.

3. A tray system according to claim 1, wherein said first sheet and/or said second sheet are arrangable to said tray by a snap locking arrangement.

4. A tray system according to claim 1, wherein said aperture has a round shape.

5. A tray system according to claim 1, wherein said first and/or second sheet is made of plastic or paper.

* * * * *